(12) United States Patent
Vilsmeier et al.

(10) Patent No.: US 7,292,037 B2
(45) Date of Patent: Nov. 6, 2007

(54) METHOD AND DEVICE FOR GENERATING A CT DATA SET

(75) Inventors: Stefan Vilsmeier, Kufstein (AT); Claus Schaffrath, München (DE); Thomas Feilkas, Grafing (DE)

(73) Assignee: BrainLAB AG, Feldkirchen (DE)

( * ) Notice: Subject to any disclaimer, the term of this patent is extended or adjusted under 35 U.S.C. 154(b) by 253 days.

(21) Appl. No.: 11/238,685

(22) Filed: Sep. 29, 2005

(65) Prior Publication Data

US 2006/0074293 A1 Apr. 6, 2006

Related U.S. Application Data

(60) Provisional application No. 60/616,988, filed on Oct. 8, 2004.

(30) Foreign Application Priority Data

Sep. 30, 2004 (EP) .................. 04023325

(51) Int. Cl.
  *G01V 3/00* (2006.01)
(52) U.S. Cl. ...................... 324/318; 324/309
(58) Field of Classification Search ........ 324/300–322; 600/407–445
  See application file for complete search history.

(56) References Cited

U.S. PATENT DOCUMENTS

| | | | | |
|---|---|---|---|---|
| 5,999,840 | A | * | 12/1999 | Grimson et al. ............ 600/424 |
| 6,266,453 | B1 | * | 7/2001 | Hibbard et al. ............ 382/294 |
| 2002/0032375 | A1 | | 3/2002 | Bauch et al. |
| 2003/0185346 | A1 | | 10/2003 | Vilsmeier |

FOREIGN PATENT DOCUMENTS

| | | |
|---|---|---|
| DE | 101 44 630 A1 | 8/2002 |
| EP | 1 348 394 A1 | 1/2003 |
| WO | 00/36565 | 6/2000 |

OTHER PUBLICATIONS

European Search Report for corresponding Application No. 04023325.6 dated Feb. 18, 2005.
Kovacic S. et al.; "Three-Dimensional Registration of PET and CT Images"; Engineering in Medicine and Biology Society, Proceedings 11th Annual Conference of the IEEE; 1989; pp. 548-549, XP010088930.
Lavallee S. et al.; "Matching of Medical Images for Computed and Robot Assisted Surgery"; Engineering in Medicine and Biology Society, 1991. vol. 13: 1991., Proceedings of the Annual International Conference of the IEEE Orlando, FL, Oct. 31, 1991; pp. 39-40, XP010101564.

(Continued)

*Primary Examiner*—Brij Shrivastav
(74) *Attorney, Agent, or Firm*—Renner, Otto, Boisselle and Sklar, LLP

(57) ABSTRACT

A method and device generating a computer tomography data set CT* of an object, wherein a nuclear spin tomography recording MR of said object is obtained, and a transformation or mapping protocol $f(MR_R)$ for a nuclear spin tomography reference data set $MR_R$ is ascertained. The nuclear spin tomography reference data set $MR_R$ can be mapped onto said recorded nuclear spin tomography data set MR, wherein said ascertained transformation or mapping protocol f is applied to a computer tomography reference data set $CT_R$ corresponding to the nuclear spin tomography reference data set $MR_R$ to determine a virtual computer tomography data set $CT^* = f(CT_R)$.

11 Claims, 3 Drawing Sheets

OTHER PUBLICATIONS

Fookes C. et al.; Institute of Electrical and Electronics Engineers: "The Use of Mutual Information for Rigid Medical Image Registration: A Review"; IEEE 2002 International Conference on Systems, Man and Cybernetics. Yasmine Hammamet, Tunesia, Oct. 6-9, 2002; IEEE International Conference on Systems, Man and Cybernetics, New York, NY: IEEE, US, Bd. vol. 7 of 7, Oct. 6, 2002; pp. 689-694, XP010623558.

Sorlie C. et al.; Matching of Digitised Brain Atlas to Magnetic Resonance Images; Medical and Biological Engineering and Computing, Peter Peregrinus Ltd. Stevenage, GB, Bd. 35, Nr. 3, May 1997; pp. 239-245, XP000677432.

Vaillant M. et al.; "H.ierarchical Matching of Cortical Features of Deformable Brain Image Registration"; Information Processing in Medical Imaging. 16$^{th}$ International Conference, IPMI 1999. Proceedings (Lecture Notes in Computer Science vol. 1613) Springer-Verlag Berlin, Germany, 1999; pp. 182-195, XP002318431.

* cited by examiner

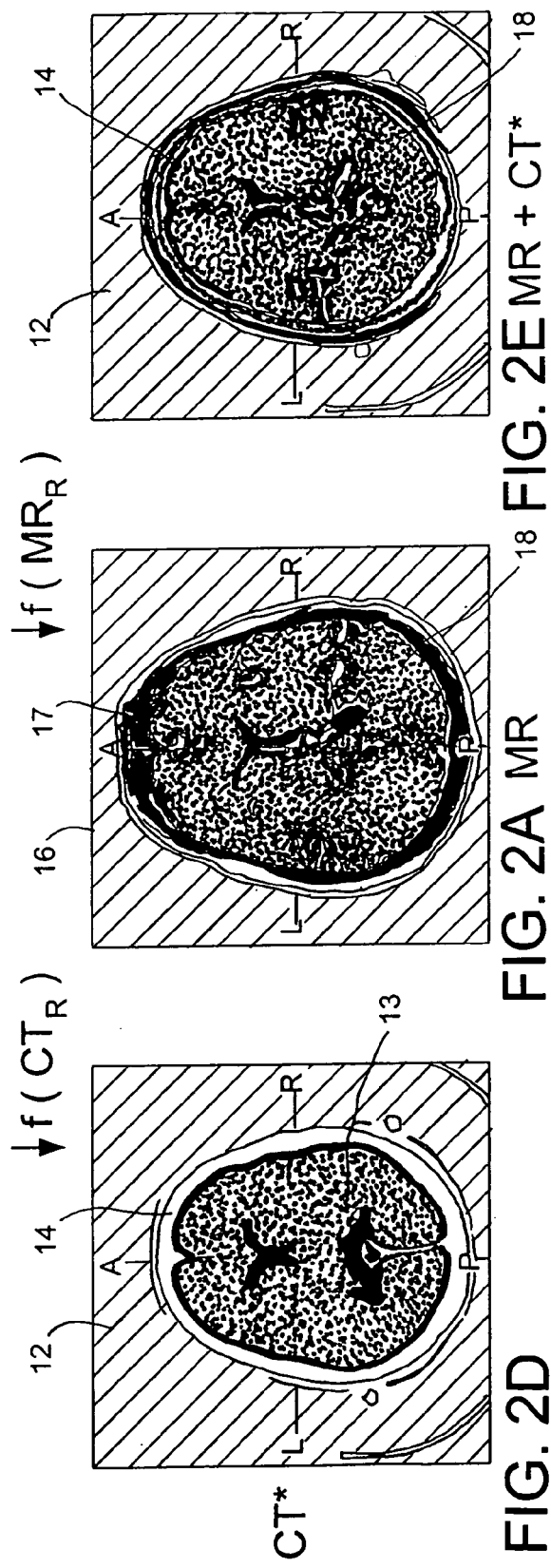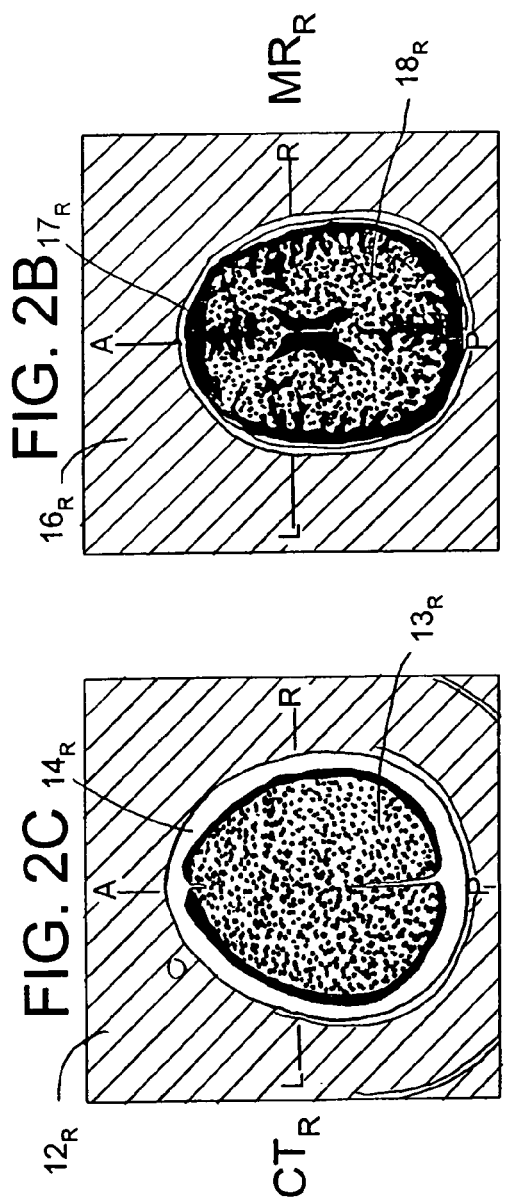

METHOD AND DEVICE FOR GENERATING A CT DATA SET

RELATED APPLICATION DATA

This application claims priority of U.S. Provisional Application No. 60/616,988 filed on Oct. 8, 2004, which is incorporated herein by reference in its entirety.

FIELD OF THE INVENTION

The present invention relates to a method and device for generating a computer tomography (CT) data set of an object and, more particularly, to a virtual CT data set (i.e., a data set not produced by a CT recording) of a body structure such as, for example, the head, hip or spine.

BACKGROUND OF THE INVENTION

When examining a patient or preparing for surgery, in particular surgery in the area of bones (e.g., a spine, hip joint or knee operation), computer tomography recordings of the body structure in question are obtained. Using the CT images, the body structure in question can be analyzed prior to and/or during the surgical procedure. Generally, CT images of bone structures are obtained using x-ray images. X-ray images, however, require that the patient be subjected to x-ray radiation, which can be detrimental to the patient's health.

Nuclear spin tomography recordings (MRI), which can be obtained without a detrimental affect to the patient's health, are suitable for displaying soft tissue. MRI, however, produces poor images of bone structure, and many times the bone structure cannot be identified in the image.

SUMMARY OF THE INVENTION

The present invention enables the generation of a data set for determining a bone structure with minimal to no detrimental affect on the patient's health. The data set generated in accordance with the invention can be a virtual computer tomography data set or the like.

A method is provided for generating a data set for locating a bone. The data set, for example, can be a three-dimensional computer tomography data set, a three-dimensional mapping or a representation of the bone structure present in the body of a patient. A nuclear spin resonance recording MR of a body part or body structure of the patient, such as a hip, can be obtained using conventional techniques. Furthermore, a generic or MRI reference data set $MR_R$ for the recorded body part or recorded body structure, such as, for example, a magnetic resonance recording of a reference hip, can be used together with a generic or computer tomography reference data set $CT_R$ of said body structure, e.g., the reference hip. Such reference data sets, for example, can be previously stored in a database prior to obtaining the recording of the body or body structure MR. The reference data sets can have a known positional relationship to each other, e.g., they can be fused. Such reference data sets already exist for all body or bone structures.

A transformation or mapping protocol can be ascertained using an algorithm known in the prior art, such as described in M. Vaillant and C. Davatzikos, "Hierarchical Matching of Cortical Features for Deformable Brain Image Registration", IP-MI '99, Volume 1613, pages 182-195, June 1999, J. C. Gee and M. Reivich and R. Bajcsy, "Elastically Deforming 3D Atlas to Match Anatomical Brain Images", J. Comp. Assist. Tomogr., Volume 17, pages 225-236, 1993 or DE 101 44 630 A1, which is owned by the assignee of the present invention. The Vaillant et al. and Gee et al. articles and DE 101 44 630 A1 are hereby incorporated by reference in their entireties.

In other words, a morphing method can be performed such that the nuclear spin tomography reference data set $MR_R$ can be mapped onto the recorded nuclear spin tomography data set MR by means of a mapping protocol f defined by Equation. 1.

$$f(MR_R)=MR \qquad \text{Equation 1}$$

In Equation 1, f is a function or mapping protocol of a three-dimensional space and describes how the nuclear spin tomography reference data set $MR_R$ can be deformed to obtain the nuclear spin tomography data set MR of the body part or structure in question. The mapping protocol f ascertained in this way can be applied to the computer tomography reference data set $CT_R$, which can be assigned to the nuclear spin tomography reference data set $MR_R$ to obtain a three-dimensional virtual computer tomography data set CT*. The three-dimensional virtual computer tomography data set CT*, for example, can describe the bone structure of the object of which only a nuclear spin resonance recording MR has been obtained, without a radiation burden to the patient.

Calculating the computer tomography data set CT* can be described by Equation 2.

$$CT^*=f(CT_R) \qquad \text{Equation 2}$$

The function f used to transform the computer tomography reference data set $CT_R$ and which describes a transformation in three-dimensional space is the transformation or function described above. Thus, a "virtual" computer tomography data set CT* can be generated without performing a computer tomography recording.

The method thus enables a computer tomography recording to be obtained for a patient, without a radiation burden to the patient. Both the calculated computer tomography data set CT* and the recorded nuclear spin tomography data set MR are provided such that a combination of these data sets can be generated by fusion. This provides information with respect to the bone structure and with respect to soft tissue in a single data set, which can be used, for example, for examining a patient or planning surgery.

Preferably, a computer tomography reference data set $CT_R$ and/or nuclear spin resonance reference data set $MR_R$ are used which are segmented and labeled (e.g., for the reference data set in question it is known where the individual body structures, such as bone tissue or soft tissue, are delineated as well as the tissue type). Once the transformation or mapping function f has been determined, this information can be transferred from a reference data set to the nuclear spin resonance data set MR or to the virtual computer tomography data set CT*.

In order to register the recorded body part, known fluoromatching can be performed, wherein the virtual computer tomography data set CT* is used as a DRR (digital reconstructed radiograph) representation. It is thus possible to perform so-called MR-to-fluoro matching, even intra-operatively, wherein a three-dimensional data set is registered using one or more two-dimensional x-ray recordings, such as described in U.S. Pat. No. 4,791,934, which is incorporated herein by reference in its entirety. The CT data set can equally be registered using other methods, such as paired-point matching or similar feature-based algorithms.

If the parameters in the computer tomography recording MR of a patient or body structure are different from the parameters used in the reference nuclear spin resonance recording $MR_R$, then a mapping protocol or function can be ascertained or specified. The mapping protocol or function can produce from one of the two nuclear spin resonance recordings a data set that can be compared with the other nuclear spin resonance recording to ascertain the mapping or transformation protocol $f(MR_R)=MR$.

The invention further provides a navigation method, wherein a virtual computer tomography data set CT* ascertained in accordance with the invention is used to navigate an object or instrument using a known navigation system.

The invention also provides a computer program which, when it is loaded onto a computer or is running on a computer, performs a method such as described above, and to a program storage medium or computer program product comprising such a computer program.

The invention also provides a device for generating a computer tomography data set CT* and can include: a nuclear spin tomograph for generating a nuclear spin tomography recording MR of a body or body structure; a database in which a nuclear spin tomography reference data set $MR_R$ and a computer tomography reference data set $CT_R$ which is assigned to the nuclear spin tomography reference data set $MR_R$ can be stored; and a computational unit from which a mapping protocol $f(MR_R)$ can be ascertained or calculated, wherein the nuclear spin tomography reference data set $MR_R$ can be mapped onto the recorded nuclear spin tomography data set MR using the mapping protocol, such that a virtual computer tomography data set CT* can be ascertained by transforming the computer tomography reference data set $CT_R$ corresponding to the nuclear spin tomography reference data set $MR_R$ using $CT^*=f(CT_R)$.

The device preferably is coupled to an output or display unit, such as a screen or the like, on which the recorded nuclear spin resonance data set MR and the virtual computer tomography data set CT* can be displayed.

The device preferably is connected to a navigation system, wherein the body structure recorded by means of a nuclear spin tomography method can be registered and a known navigation method can be performed.

The forgoing and other embodiments of the invention are hereinafter discussed with reference to the drawings.

BRIEF DESCRIPTION OF THE DRAWINGS

FIGS. 2A-2E are schematic representations of a method in accordance with the invention, on the basis of recording a head in a predetermined plane.

DETAILED DESCRIPTION

Figure 1:
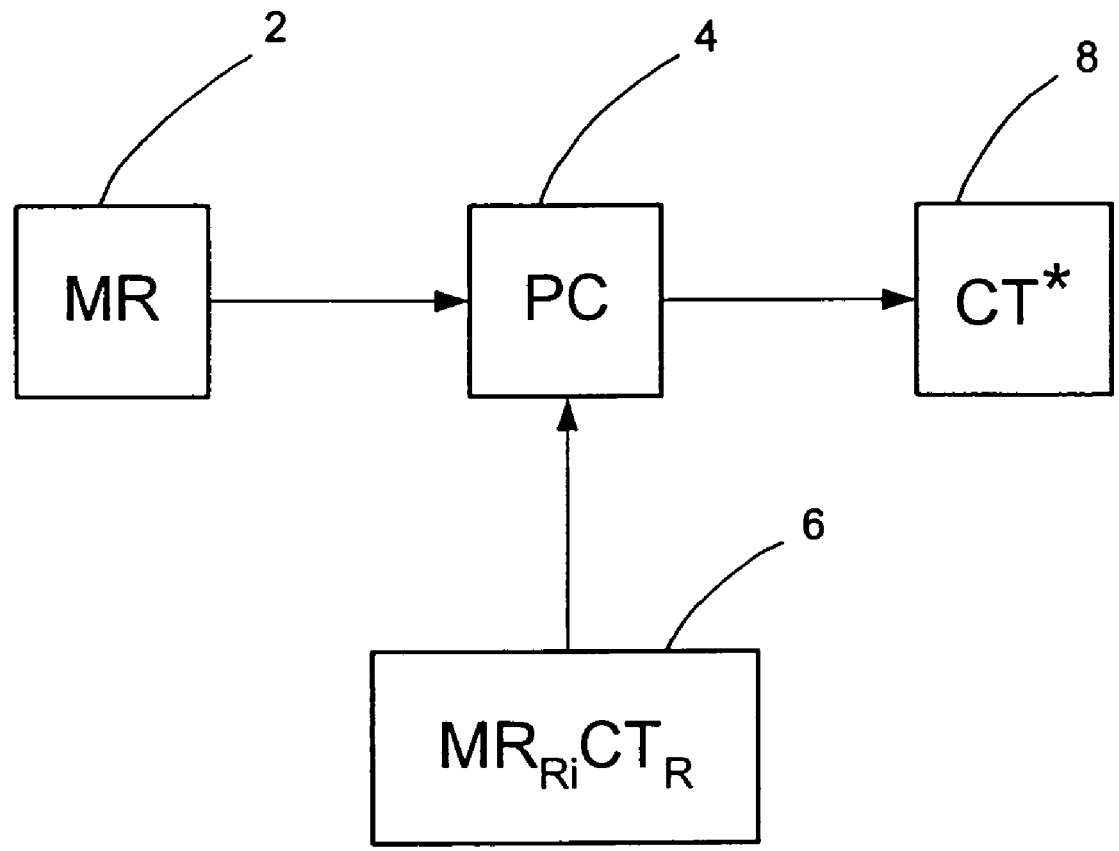
FIG. 1 is a schematic representation of a device in accordance with the invention.

FIG. 1 illustrates a nuclear spin tomograph 2 that can be used to obtain or record a nuclear spin tomography recording MR of a body or body structure of a patient. The data recorded by the nuclear spin tomograph MR describe a three-dimensional structure of the body and can be relayed or communicated to a computational unit 4. The computational unit 4 includes or has access to a database 6 in which a nuclear spin tomography reference data set $MR_R$ and a computer tomography reference data set $CT_R$ (preferably segmented and labeled) are stored. A virtual computer tomography data set CT* 8 is ascertained from the data sets MR, $MR_R$ and $CT_R$ using the method as described herein, and can be fused with the recorded computer tomography data set MR and used as the basis for a planning and/or navigation method.

FIG. 2A illustrates an exemplary recorded nuclear spin resonance data set MR of an incision plane of a patient's head, wherein the area 16 corresponds to air around the head. Within the head, the areas 17 correspond to bone tissue or other elements such as, for example, air. The areas 18 represent soft tissue, such as, for example, the brain. The reference image or nuclear spin resonance reference data set $MR_R$ of FIG. 2B, which can be stored for example in the database 6, similarly shows the reference areas 16R, 17R and 18R corresponding to the areas 16, 17 and 18 of FIG. 2A, wherein the structure or shape of the respective areas in the reference data set $MR_R$ can be different from the recorded data set MR. Using a known method, a transformation or mapping protocol f is ascertained, from which the reference data set $MR_R$ can be mapped onto recorded data set MR using the mapping $f(MR_R)=MR$.

The computer tomography reference data set $CT_R$ shown in FIG. 2C is a recording of the same incision plane of the reference head used for the reference data set $MR_R$. Thus, the computer tomography reference data set $CT_R$ corresponds to the incision plane of the computer tomography reference data set $MR_R$ and is segmented and labeled (e.g., it is known what course the bone structures in the reference data set take and how they are delineated from each other). The area 12R outside the head indicates air present around the head. The white area 14R corresponds to bone tissue and the area 13R corresponds to soft tissue. The computer tomography reference data set $CT_R$, unlike the nuclear spin resonance reference data set $MR_R$, contains a clear delineation of the bone tissue 14R and its structure.

The transformation or mapping function f described above is used to transform the computer tomography reference data set $CT_R$ into the virtual computer tomography data set CT* of FIG. 2D using the mapping $CT^*=f(CT_R)$. As a result, a computer tomography data set can be obtained that corresponds to a computer tomography recording of a body or object of which only a nuclear spin resonance recording MR has been obtained.

The nuclear spin resonance data set MR and the virtual computer tomography data set CT* can be fused into a joint data set MR+CT*, as shown in FIG. 2E, such that detailed structural information on the soft and hard or bone tissue is simultaneously contained in the fused data set.

Figure 3:
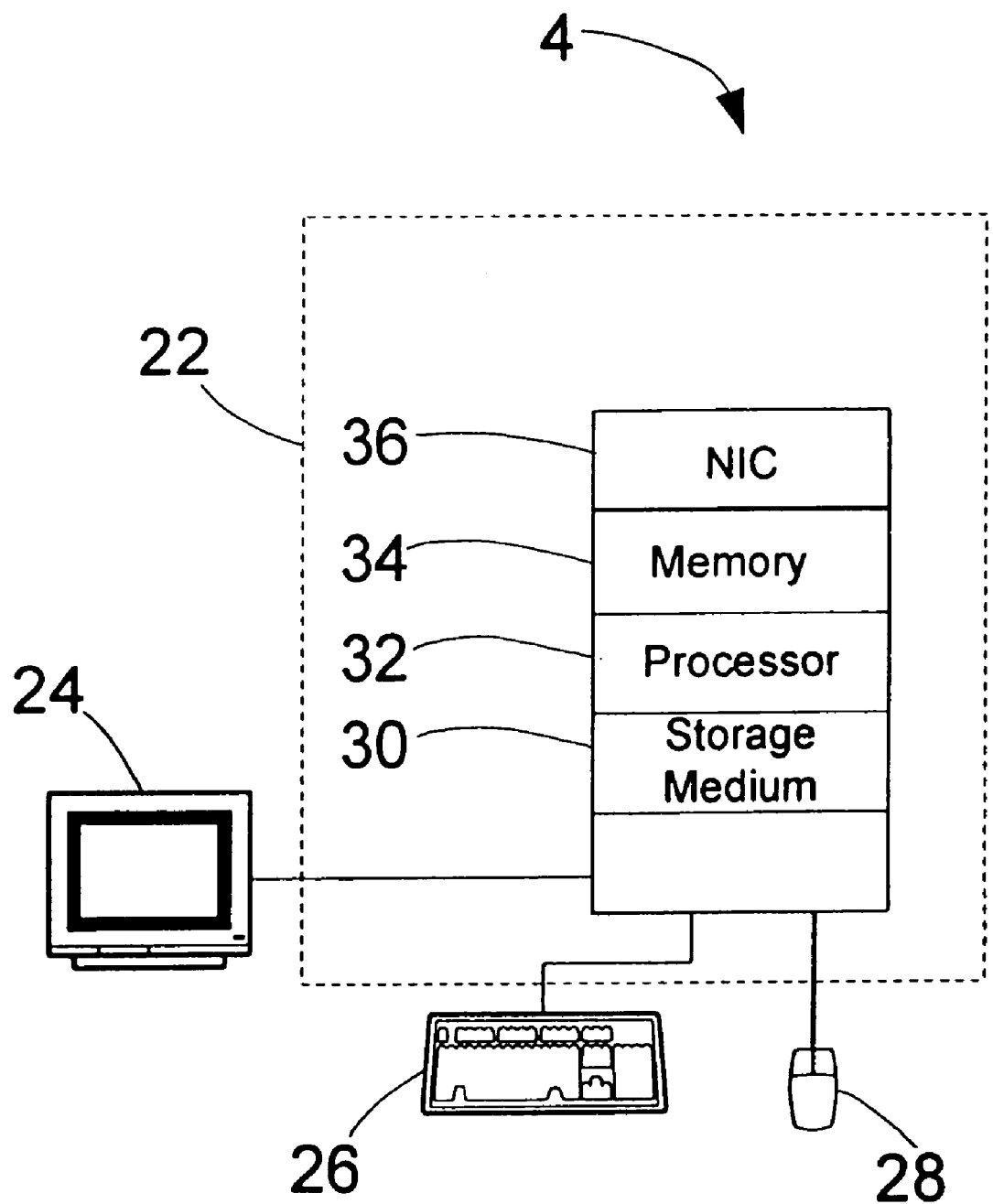
FIG. 3 is a diagrammatic illustration of a computer system that can be used to implement the method of the present invention.

Moving to FIG. 3, an exemplary computational unit 4 for executing a computer program in accordance with the present invention is illustrated. The computational unit 4 includes a computer 22 for processing data, and a display 24 (e.g., a Cathode Ray Tube, Liquid Crystal Display, or the like) for viewing system information. A keyboard 26, pointing device 28 or input and/or output device may be used for data entry, data display, screen navigation, etc. The keyboard 26 and pointing device 28 may be separate from the computer 22 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 26 and pointing device 28. Touch screens may be beneficial when the available space for a keyboard 26 and/or a pointing device 28 is limited.

Included in the computer 22 is a storage medium 30 for storing information, such as application data, screen information, programs, etc. The storage medium 30 may be a hard drive, an optical drive, or the like. A processor 32, such as an AMD Athlon 64™ processor or an Intel Pentium IV® processor, combined with a memory 34 and the storage medium 30 execute programs to perform various functions, such as data entry, numerical calculations, screen display, system setup, etc. A network interface card (NIC) 36 allows the computer 22 to communicate with external devices.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system for generating a computer tomography data set of an object, wherein a nuclear spin tomography recording MR of said object has been obtained, comprising:
   a processor circuit having a processor and a memory;
   a mapping subsystem stored in the memory and executable by the processor, the subsystem comprising:
   logic that ascertains a transformation or mapping protocol $f(MR_R)$ for a nuclear spin tomography reference data set, wherein said nuclear spin tomography reference data set can be mapped onto said recorded nuclear spin tomography data set; and
   logic that applies said ascertained transformation or mapping protocol f to a computer tomography reference data set corresponding to the nuclear spin tomography reference data set to determine a virtual computer tomography data set $CT^*=f(CT_R)$.

2. A method for generating a computer tomography data set of an object, comprising:
   obtaining a nuclear spin tomography recording of said object;
   ascertaining a transformation or mapping protocol $f(MR_R)$ for a nuclear spin tomography reference data set, wherein said nuclear spin tomography reference data set can be mapped onto said recorded nuclear spin tomography data set; and
   wherein said ascertained transformation or mapping protocol f is applied to a computer tomography reference data set corresponding to the nuclear spin tomography reference data set to determine a virtual computer tomography data set $CT^*=f(CT_R)$.

3. The method as set forth in claim 2, further comprising fusing the recorded nuclear spin resonance data set MR and the virtual computer tomography data set.

4. The method as set forth in claim 2, further comprising using a segmented and/or labeled nuclear spin resonance reference data set and/or computer tomography reference data set.

5. The method as set forth in claim 2, further comprising registering the recorded object by fluoro-to-CT matching using the virtual computer tomography data set.

6. The method as set forth in claim 2, further comprising using a conversion protocol to convert the nuclear spin resonance reference data set and/or the recorded nuclear spin tomography data set such that the recorded nuclear spin resonance data set and the nuclear spin tomography reference data set can be compared if different parameters have been used to generate the nuclear spin resonance data sets.

7. A method for navigating an object or body, wherein a virtual computer tomography data set, ascertained as set forth in claim 2, is used for navigating.

8. A program embodied in a computer-readable medium for generating a computer tomography data set of an object, wherein a nuclear spin tomography recording of said object has been obtained, comprising:
   code that ascertains a transformation or mapping protocol $f(MR_R)$ for a nuclear spin tomography reference data set, wherein said nuclear spin tomography reference data set can be mapped onto said recorded nuclear spin tomography data set; and
   code that applies said ascertained transformation or mapping protocol (f) to a computer tomography reference data set corresponding to the nuclear spin tomography reference data set to determine a virtual computer tomography data set $CT^*=f(CT_R)$.

9. A device for generating a computer tomography data set, comprising:
   a nuclear spin tomograph for generating a nuclear spin tomography recording of a body or body structure;
   a database in which a nuclear spin tomography reference data set and a computer tomography reference data set are stored, wherein the computer tomography reference data set corresponds to the nuclear spin tomography reference data set; and
   a computational unit adapted to ascertain or calculate a transformation or mapping protocol $f(MR_R)$, wherein said transformation or mapping protocol defines a mapping of the nuclear spin tomography reference data set onto the recorded nuclear spin tomography data set, said computational unit also adapted to calculate or transform a virtual computer tomography data set from said computer tomography reference data set using the ascertained mapping protocol f.

10. The device as set forth in claim 9, comprising an output or display unit for displaying the virtual computer tomography data set and/or the recorded nuclear spin resonance data set.

11. The device as set forth in claim 9, comprising a navigation system for navigating an object, body or instrument.

* * * * *